US011526985B1

(12) United States Patent
Welch

(10) Patent No.: US 11,526,985 B1
(45) Date of Patent: Dec. 13, 2022

(54) METHOD AND APPARATUS FOR IMPROVING THE SPATIAL RESOLUTION IN MOLECULAR BREAST TOMOSYNTHESIS

(71) Applicant: SMART BREAST CORPORATION, Sherman Oaks, CA (US)

(72) Inventor: Benjamin Welch, Hampton, VA (US)

(73) Assignee: SMART BREAST CORPORATION, Sherman Oaks, CA (US)

( * ) Notice: Subject to any disclaimer, the term of this patent is extended or adjusted under 35 U.S.C. 154(b) by 266 days.

(21) Appl. No.: 16/892,685

(22) Filed: Jun. 4, 2020

Related U.S. Application Data

(60) Provisional application No. 62/857,944, filed on Jun. 6, 2019.

(51) Int. Cl.
| | |
|---|---|
| *G06K 9/00* | (2022.01) |
| *A61B 5/00* | (2006.01) |
| *G06T 7/00* | (2017.01) |
| *G06T 5/00* | (2006.01) |
| *A61B 6/00* | (2006.01) |

(Continued)

(52) U.S. Cl.
CPC ............ *G06T 7/0012* (2013.01); *A61B 6/025* (2013.01); *A61B 6/037* (2013.01); *A61B 6/06* (2013.01); *A61B 6/12* (2013.01); *A61B 6/4258* (2013.01); *A61B 6/44* (2013.01); *A61B 6/466* (2013.01); *A61B 6/502* (2013.01); *G06T 5/003* (2013.01); *G06T 2207/10112* (2013.01); *G06T 2207/30068* (2013.01)

(58) Field of Classification Search
CPC .................................. G06K 9/00; A61B 90/17

USPC ....... 382/100, 103, 123, 128–133, 154, 162, 382/168, 181, 199, 214, 232, 254, 285, 382/305; 235/383; 600/436, 410; 606/130
See application file for complete search history.

(56) References Cited

U.S. PATENT DOCUMENTS

| | | | |
|---|---|---|---|
| 11,096,636 B2 * | 8/2021 | Kross ................. | A61B 6/502 |
| 2002/0125313 A1 * | 9/2002 | Broff ................. | G06Q 30/02 |
| | | | 235/383 |

(Continued)

OTHER PUBLICATIONS

Opan,Olga.etal.,MolecularImagingoftheBreastUsingaVariable-AngleSlant-HoleCollimator,IEEETrans.Nucl.ci.61(3), 1143-1152(2014). (Year: 2014).*

(Continued)

*Primary Examiner* — Seyed H Azarian
(74) *Attorney, Agent, or Firm* — Bartony & Associates, LLC

(57) ABSTRACT

An apparatus and method for reducing the blurriness of tomographic (3D) images constructed from a gamma camera system with one or more VASH (variable-angle slant-hole) collimators. A conventional gamma camera with a VASH collimator exhibits a loss of spatial resolution from the fact that the gamma-ray is entering the detector element at an angle other than normal to the surface. This depth dependence of the spatial localization causes a blurring of the spatial resolution, which is dependent on the incident angle relative to the normal, on the thickness of the detector element and on the stopping length of the gamma-ray in the detector element material. The invention provides an apparatus and method for correcting the spatial location where the gamma ray is recorded to improve the spatial resolution of the system.

8 Claims, 5 Drawing Sheets

Block diagram showing steps to determine the true pixel location of the gamma event.

(51) Int. Cl.
*A61B 6/02* (2006.01)
*A61B 6/06* (2006.01)
*A61B 6/12* (2006.01)
*A61B 6/03* (2006.01)

(56) References Cited

U.S. PATENT DOCUMENTS

| | | | |
|---|---|---|---|
| 2010/0016865 A1* | 1/2010 | Kieper ................. | A61B 6/4258 606/130 |
| 2013/0158389 A1* | 6/2013 | O'Connor .............. | A61B 90/17 600/436 |
| 2018/0310897 A1* | 11/2018 | Hugg ................... | A61B 6/0414 |

OTHER PUBLICATIONS

Gilland, D. et al.. Evaluation of a novel collimator for molecular breast tomosynthesis, Med. Phys. 44 (11), 5740-5766 (2017).
Gopan, Olga. et al., Molecular Imaging of the Breast Using a Variable-Angle Slant-Hole Collimator, IEEE Trans. Nucl. Sci. 61 (3), 1143-1152 (2014).
More, M., et al., Limited Angle Dual Modality Breast Imaging, IEEE Trans. Nucl. Sci. 54 (3), 504-513 (2007).
Welch, BL et al., Gamma-Guided Stereotactic Breast Biopsy System, IEEE Trans. Nucl. Sci. 53 (5), 2690-2697, (2006).
Welch, BL et al.,Quality Assurance Procedure for a Gamma Guided Stereotactic Breast Biopsy System, Physica Medica 21, 94 (2006).

\* cited by examiner

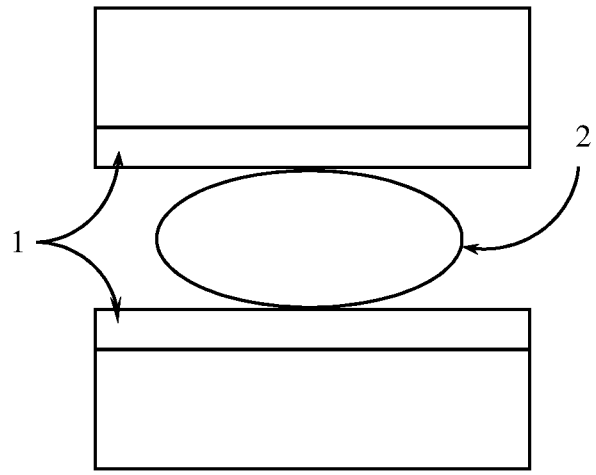
Figure 1 – Drawing of MBT system showing detectors (1) and breast (2).
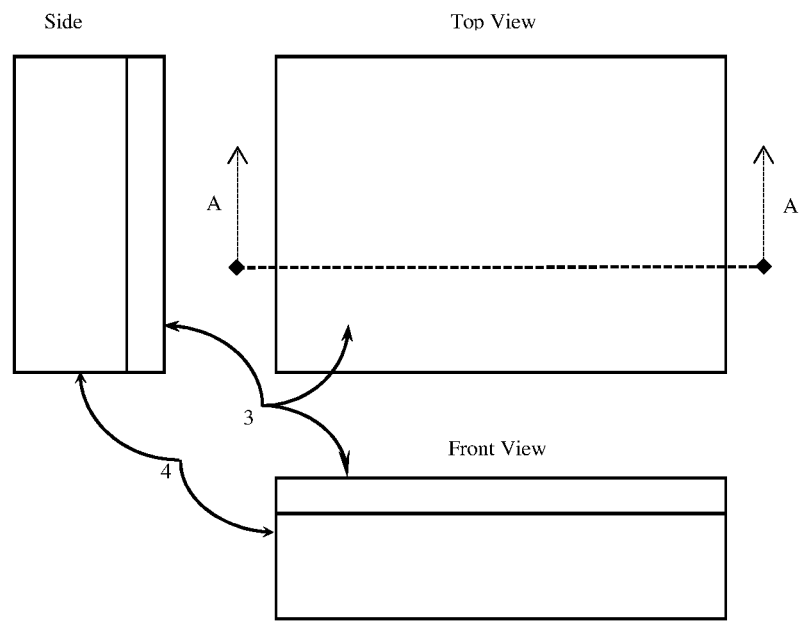
Figure 2 – Drawing of gamma-camera showing collimator (3) and detector (4) from Top View, Front View and Side View.

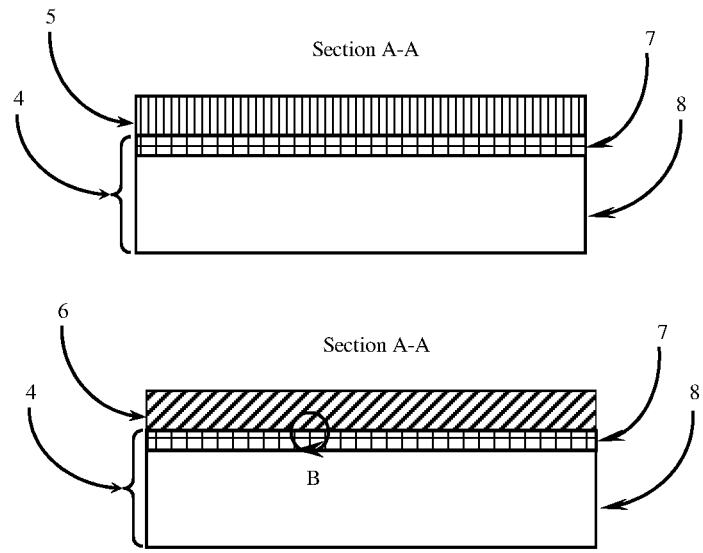

Figure 3 – Drawing showing internal features of gamma-camera across Section AA from Figure 2 for both parallel-hole collimator (5) and slant-hole collimator (6). Also indicated are direct conversion detector element (7) and electronics (8).

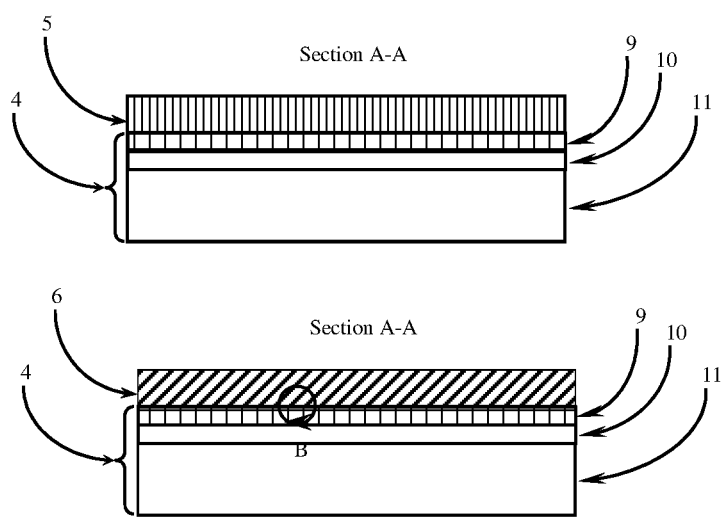

Figure 4 – Drawing showing internal features of gamma-camera across Section AA from Figure 1 for both parallel-hole collimator (5) and slant-hole collimator (6). Also indicated are indirect conversion detector element (9), light sensor (10) and electronics (11).

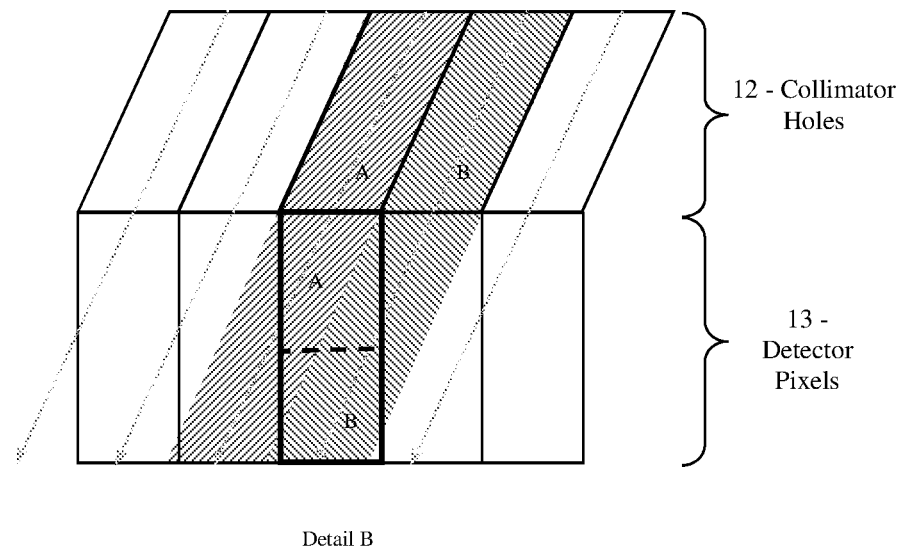

Detail B

Figure 5 - Equal collimator hole and detector element pixel size (low aspect ratio pixels). Horizontal dash line separates regions of the pixel primarily from collimator hole A (top) and B (bottom).

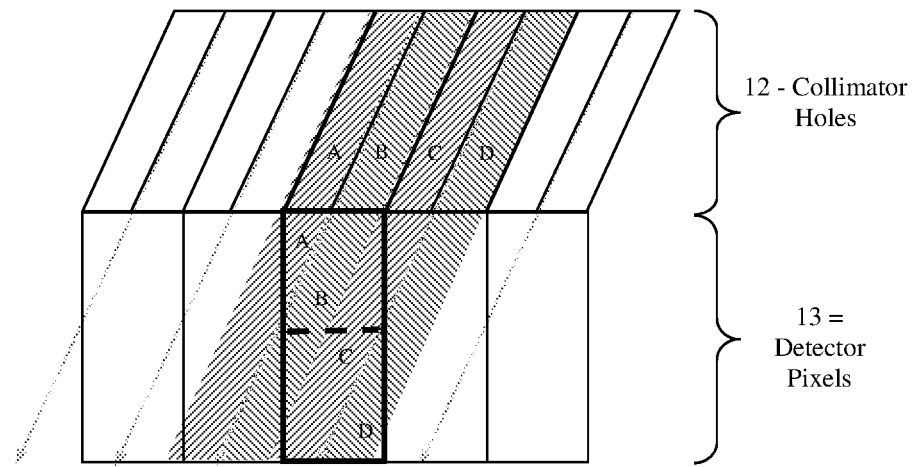

Detail B

Figure 6 - Collimator hole less than detector element pixel size (low aspect ratio pixels). Horizontal dash line separates regions of the pixel primarily from collimator hole B (top) and C (bottom).

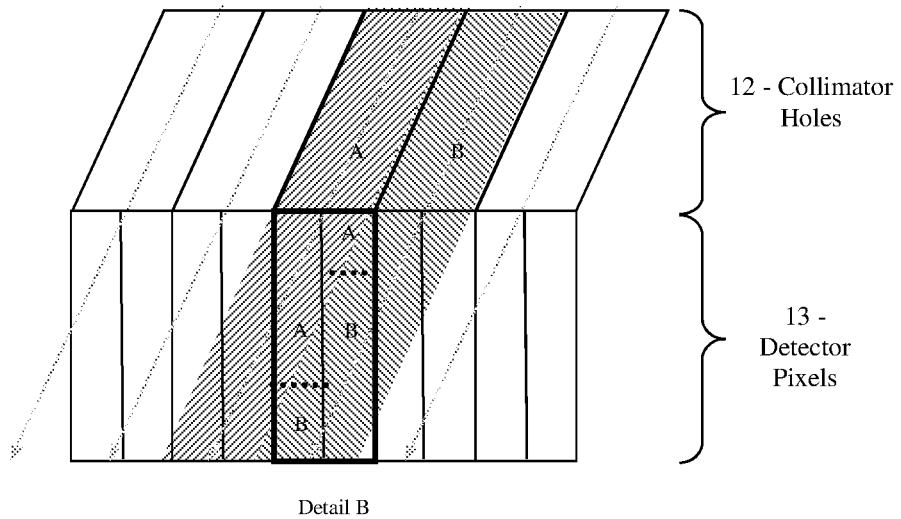

Detail B

Figure 7 - Collimator hole larger than detector element pixel size (high aspect ratio pixels). Horizontal dash lines separate regions of the left-hand pixel primarily from collimator hole A (top) and B (bottom) and of the right-hand pixel primarily from the collimator hole A (top) and B (bottom).

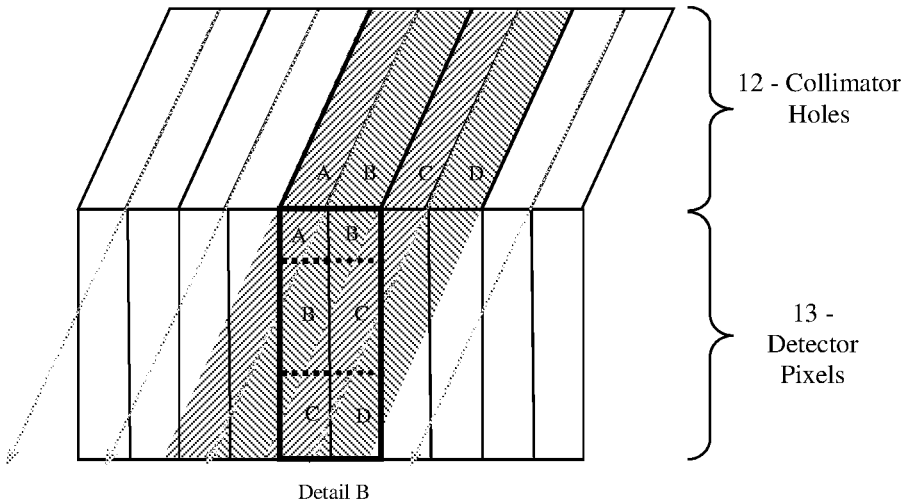

Detail B

Figure 8 - Equal collimator hole and detector element pixel size (high aspect ratio pixels). Horizontal dash lines separate regions of the left-hand pixel primarily from collimator hole A (top), B (middle) and C (bottom) and of the right-hand pixel primarily from collimator hole B (top), C (middle) and D (bottom).

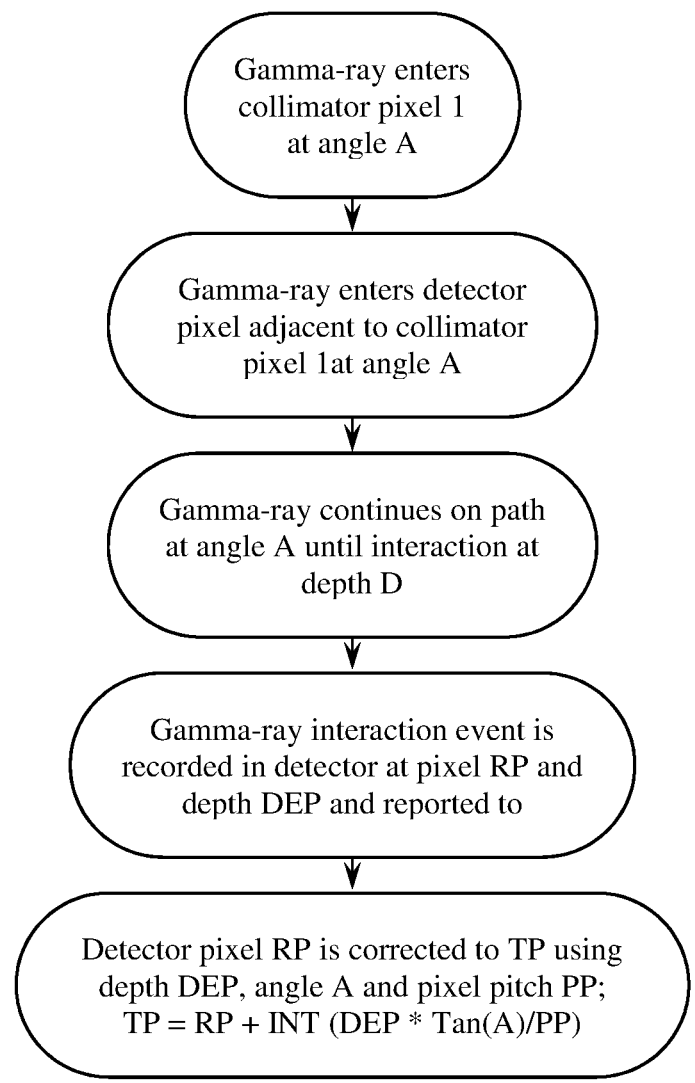
Figure 9 Block diagram showing steps to determine the true pixel location of the gamma event.

METHOD AND APPARATUS FOR IMPROVING THE SPATIAL RESOLUTION IN MOLECULAR BREAST TOMOSYNTHESIS

This application claims the benefit of Provisional U.S. Patent Application Ser. No. 62/857,944 filed Jun. 6, 2019, the contents of which are incorporated herein in its entirety.

FIELD OF THE INVENTION

The present invention relates to the diagnosis of cancer in breast tissue and more particularly to an apparatus and method for correcting for the blurring of the spatial location in a gamma camera molecular breast tomosynthesis system.

BACKGROUND OF THE INVENTION

Unlike a conventional gamma camera with a parallel hole collimator where the gamma-rays enter the detector element normal to the surface, a gamma camera with a variable-angle slant-hole (VASH) collimator suffers a loss of spatial resolution from the fact that the gamma-ray is entering the detector element at an angle other than normal to the surface.

Unfortunately, using a VASH collimator results in the spatial location where the gamma-ray that is recorded is dependent on the depth that the gamma-ray penetrates into the detector element before it is recorded. The further the gamma-ray penetrates, the further the location that is recorded is from the location where the gamma-ray entered the detector element. This depth dependence of the spatial localization causes a blurring of the spatial resolution, which is dependent on the incident angle relative to the normal, on the thickness of the detector element and on the stopping length of the gamma-ray in the detector element material. Accordingly a method is needed to correct for this blurring of the spatial location where the gamma ray is recorded to improve the spatial resolution of the system.

SUMMARY OF THE INVENTION

The invention is an apparatus and method for reducing the blurriness of tomographic (3D) images constructed from a gamma camera system with one or more VASH (variable-angle slant-hole) collimators. A conventional gamma camera with a VASH collimator exhibits a loss of spatial resolution from the fact that the gamma-ray is entering the detector element at an angle other than normal to the surface. This depth dependence of the spatial localization causes a blurring of the spatial resolution, which is dependent on the incident angle relative to the normal, on the thickness of the detector element and on the stopping length of the gamma-ray in the detector element material. The invention provides an apparatus and method for correcting the spatial location where the gamma ray is recorded to improve the spatial resolution of the system.

BRIEF DESCRIPTION OF THE SEVERAL VIEWS OF THE DRAWING(S)

Reference is made herein to the accompanying drawings, which are not necessarily drawn to scale, and wherein:

FIG. 1 is a front view of a molecular breast tomosynthesis system.

FIG. 2 depicts a gamma-camera showing a collimator (3) and a detector (4) including a top view, front view and side view.

FIG. 3 depicts two conceptual views showing internal features of a gamma-camera with a solid-state element taken along line A-A of FIG. 2 including, in the top view, a parallel-hole collimator and, in the bottom view, a slant-hole collimator.

FIG. 4 depicts two conceptual views showing internal features of a gamma-camera with a scintillation crystal element taken along line A-A of FIG. 2 including, in the top view, a parallel-hole collimator, and, in the bottom view, a slant-hole collimator.

FIG. 5 is a close-up view of the collimator and detector portion of an MBT system having collimator holes and detector element pixels of equal sizes with low aspect ratio pixels. The region of this close-up view is shown in Detail B of FIGS. 3 and 4.

FIG. 6 is a close-up view of the collimator and detector portion of an MBT system having collimator holes of a size less than the detector element pixel sizes with low aspect ratio pixels. The region of this close-up view is shown in Detail B of FIGS. 3 and 4.

FIG. 7 is a close-up view of the collimator and detector portion of an MBT system having collimator holes of a size larger than the detector element pixel sizes with high aspect ratio pixels. The region of this close-up view is shown in Detail B of FIGS. 3 and 4

FIG. 8 is a close-up view of the collimator and detector portion of an MBT system having collimator holes and detector element pixels of equal sizes with high aspect ratio pixels. The region of this close-up view is shown in Detail B of FIGS. 3 and 4.

FIG. 9 is a block diagram showing the method according to the invention used to determine the true pixel location of the gamma event.

DETAILED DESCRIPTION

The current invention provides a method for correcting for the blurring of the spatial location in a molecular breast tomosynthesis system where the gamma ray is recorded to improve the spatial resolution of the system.

The method for correcting for the blurring of the spatial location in a molecular breast tomosynthesis system includes determining the depth of the gamma-ray interaction within the detector element and using that information to correct for the blurring and, as a result improving the spatial resolution. This improvement in determining the spatial location improves the spatial resolution of the reconstruction of the emission within the breast.

In Molecular Breast Tomosynthesis (MBT), as shown in FIG. 1, two gamma cameras 1 are placed on opposite sides of the breast 2 to record images. These images are taken at various angles while leaving the breast immobilized in close proximity to the gamma-cameras and a three-dimensional reconstruction of the emission within the breast is then produced from these projection images.

Referring to FIG. 2, gamma camera images are produced by using a collimator 3 to limit the solid angle of the gamma rays and a detector 4 to record the location of the gamma ray event. The collimator is typically a high-Z material covering the entrance to the detector with holes through it normal to the plane of the detector. These holes can be of various geometries; round, square, hexagonal. The holes define the solid angle that is seen by the region of the detector adjacent to each of the holes.

With reference to FIGS. 3 and 4, the holes in the collimator are usually normal to the surface of the collimator (90 degrees) and the collimator is referred to as a parallel-hole collimator 5. In the case where the holes are at an angle other than normal to the surface of the collimator (<90 degrees), the collimator is referred to as a slant-hole collimator 6 as shown in FIGS. 3 and 4.

In a molecular breast tomosynthesis system according to the present invention, the detector is composed of a gamma-ray sensitive element and associated electronics. The gamma sensitive element can be of two basic types; a solid-state element (e.g. cadmium zinc telluride—CZT) or a scintillation crystal element (e.g. thallium doped sodium-iodide—NaI(Tl)). Other types of solid-state elements and scintillation crystal elements are also available.

With reference to FIG. 3, in the case of a solid-state element, the gamma-ray interacts within the solid state element 7 and produces signals at the anode and cathode (i.e. direct conversion) which are measured by the electronics 8.

Referring to FIG. 4, in the case of the scintillation crystal element, the gamma-ray interacts within the scintillation crystal element 9 and produces a light signal which is then recorded with a light sensitive element 10 to produce a signal (i.e. indirect conversion) which is measured by the electronics 11.

With reference to FIGS. 5-8, in a molecular breast tomosynthesis system according to the invention, the typical collimator is replaced with a variable-angle slant-hole (VASH) collimator which is used to view the breast. The variable-angle slant-hole collimator is produced by a stack of very thin (0.25 mm) high-Z plates with a hole pattern similar to that of a collimator. These plates are then slid relative to one another or racked in one direction by an electro-mechanical mechanism that is controlled by a computer. This produces a collimator with an array of holes that can be positioned at any slant-angle over a given range relative to the normal for the plane of the detector. This VASH collimator allows images to be taken of the breast from various angles, and the resulting image is a projection of the breast from that angle.

Various techniques can be used to determine the depth at which a gamma-ray event occurs in a detector element. In the case of direct conversion, one example of how to determine the depth at which the gamma-ray interaction event occurs is to calculate the location from the ratio of the electrical signals on the anode and cathode. In the case of indirect conversion, an example of how the depth at which the gamma-ray event occurs can be determined is from the ratio of the light signals recorded at the top and bottom of the scintillation crystal. Other techniques can also be used to determine the depth at which the gamma-ray event occurs in both direct and indirect conversion elements.

The following examples give the effects of the off normal-axis incidence of the gamma-rays and the blurring that this has on the spatial resolution. Four scenarios will be presented in FIGS. 5-8.
  (a) equal collimator hole and detector pixel width (see FIG. 5)
  (b) collimator hole less than detector pixel width (see FIG. 6)
  (c) collimator hole larger than detector pixel width (see FIG. 7)
  (d) equal collimator hole and detector pixel width (see FIG. 8)

These figures show drawings of a (VASH) collimator with holes 12 at 25 degrees and an array of detector pixels 13 in the region indicated in Detail B from FIGS. 3 and 4. The low aspect ratio detector element pixels have a height to width aspect ratio of 2.5:1 and the high aspect ratio detector element pixel have a height to width aspect ratio of 5:1. Dotted arrows show the paths of the incident gamma-rays. The shaded areas are to highlight the paths of the gamma-rays incident through different collimator holes and the paths they make through the detector elements. The letters assigned to these highlighted paths in the collimator are also used to indicate the portion of the path that traverses the detector pixel/pixels highlighted in bold.

Referring to FIG. 5, the size of collimator hole 12 and detector element pixel 13 are equal with low aspect ratio pixels. The horizontal dashed line separates regions of the pixel primarily from collimator hole A (top) and B (bottom).

With reference to FIG. 6, the size of the collimator hole 12 is less than the size of the detector element pixel 13 (low aspect ratio pixels). The horizontal dashed line again separates regions of the pixel primarily from collimator hole B (top) and C (bottom).

With reference to FIG. 7, there is shown an arrangement in which the collimator hole 12 is larger than the size of the detector element pixel 13 (high aspect ratio pixels). The horizontal dashed lines separate regions of the left-hand pixel primarily from collimator hole A (top) and B (bottom) and of the right-hand pixel primarily from the collimator hole A (top) and B (bottom).

Referring to FIG. 8, there is shown an arrangement including an equal collimator hole 12 and detector element pixel 13 size (high aspect ratio pixels). The horizontal dashed lines separate regions of the left-hand pixel primarily from collimator hole A (top), B (middle) and C (bottom) and of the right-hand pixel primarily from collimator hole B (top), C (middle) and D (bottom).

With reference to FIG. 9, is a block diagram showing the steps in the method of the current invention for correcting the blurring of the spatial location and thus improving the spatial resolution in a molecular breast tomosynthesis system using a VASH collimator. As shown in the block diagram, the method includes determining the True Pixel location (TP) of each gamma-ray event from the Recorded Pixel location (RP), the DEPth of the gamma-ray interaction (DEP) within that recorded pixel, the Angle (A) of the holes in the slant-hole collimator, and the Pixel Pitch (PP). The True Pixel location (TP) of each gamma-ray event is then calculated from:

$$TP = RP + INT(DEP*\mathrm{Tan}(A)/PP)$$

where INT( ) is a function that returns the largest integer value less than the decimal value of the expression within the parenthesis. For example, $INT(x)=0$ for $0.0 <= x < 1.0$ 1 for $1.0 <= x < 2.0$ 2 for $2.0 <= x < 3.0$ $N$ for $N <= x < N+1$ The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated. Although the description above contains many specific descriptions, materials, and dimensions, these should not be construed as limiting the scope of the invention but as merely providing illustrations of some of the embodiments of this invention. Thus the scope of the invention should be determined by the appended claims and their legal equivalents, rather than by the examples given.

What is claimed is:

1. A method for correcting the blurring of the spatial location in a molecular breast tomosynthesis system including a variable-angle slant-hole (VASH) collimator and a gamma-ray sensitive element, comprising:
   collecting gamma ray events with the gamma-ray sensitive element while varying the angle of the VASH collimator;
   recording the recorded pixel location (RP), the depth of the gamma-ray interaction (DEP) within the recorded pixel, the angle (A) of the holes in the slant-hole collimator, and the pixel pitch (PP); and
   calculating the True Pixel location (TP) of each gamma-ray event according to the equation $$TP = RP + INT(DEP*Tan(A)/PP);$$

where INT (DEP*Tan(A)/PP) is a function that returns the largest integer value less than the decimal value of the expression within the parenthesis.

2. The method of claim 1 wherein the gamma-ray sensitive element is a solid-state element; and the method further comprises calculating the depth from the ratio of the electrical signals on an anode and a cathode of the solid state element.

3. The method of claim 1 wherein the gamma-ray sensitive element is a scintillation crystal element; and the method further comprises calculating the depth from the ratio of the light signals recorded at the top and bottom of the scintillation crystal.

4. A molecular breast tomosynthesis system for producing three-dimensional (3D) images with correction for blurring of spatial location, comprising:
   at least one gamma camera comprising a collimator system, a gamma-ray sensitive element to collect gamma ray events and electronics in operative connection with the gamma-ray sensitive element, said collimator system comprising a variable-angle slant-hole (VASH) collimator including a plurality of holes which are adjustable together to an angle (A) over a range of various angles; and
   an electro-mechanical mechanism to control and record the angle (A) of the plurality of holes in the VASH collimator; and
   a computer configured to record the characteristics of each gamma ray event, said characteristics comprising the pixel location (RP) of a gamma-ray event, a depth of the gamma-ray interaction (DEP) within the recorded pixel, and the angle (A) of the holes in the VASH collimator, and the pixel pitch (PP), said computer further configured to calculate a True Pixel location (TP) of each gamma-ray event according to the equation:

$$TP = RP + INT(DEP*Tan(A)/PP):$$

wherein TNT (DEP*Tan(A)/PP) is a function that returns the largest integer value less than the decimal value of the expression within the parenthesis.

5. The molecular breast tomosynthesis system of claim 4 wherein the gamma-ray sensitive element is a solid-state element and the depth of the gamma-ray interaction is calculated from the ratio of the electrical signals on an anode and a cathode of the solid-state element.

6. The molecular breast tomosynthesis system of claim 5 wherein the solid-state element is cadmium zinc telluride (CZT).

7. The molecular breast tomosynthesis system of claim 4 wherein the gamma-ray sensitive element is a scintillation crystal element, and the depth of the gamma-ray interaction is calculated from the ratio of the light signals recorded at the top and the bottom of the scintillation crystal element.

8. The molecular breast tomosynthesis system of claim 7, wherein the scintillation crystal element is thallium doped sodium-iodide (NaI(Tl)).

* * * * *

UNITED STATES PATENT AND TRADEMARK OFFICE
CERTIFICATE OF CORRECTION

| | |
|---|---|
| PATENT NO. | : 11,526,985 B1 |
| APPLICATION NO. | : 16/892685 |
| DATED | : December 13, 2022 |
| INVENTOR(S) | : Benjamin Welch |

It is certified that error appears in the above-identified patent and that said Letters Patent is hereby corrected as shown below:

In the Claims

Column 6, Claim 4, Line 20 delete "TNT (DEP*Tan(A)/PP)" and insert --INT (DEP*Tan(A)/PP)--.

Signed and Sealed this
Eleventh Day of April, 2023

Katherine Kelly Vidal
*Director of the United States Patent and Trademark Office*